United States Patent
Storm et al.

(10) Patent No.: US 10,238,102 B2
(45) Date of Patent: Mar. 26, 2019

(54) CONTROL OF ARTHROPODS IN ANIMAL ENVIRONMENTS

(75) Inventors: Clare Gillian Storm, Winchester (GB); Nicola Jane Huggett, Winchester (GB)

(73) Assignee: Exosect Limited, Winchester, Hants (GB)

( * ) Notice: Subject to any disclaimer, the term of this patent is extended or adjusted under 35 U.S.C. 154(b) by 160 days.

(21) Appl. No.: 13/640,525

(22) PCT Filed: Apr. 12, 2011

(86) PCT No.: PCT/GB2011/000572
§ 371 (c)(1),
(2), (4) Date: Dec. 11, 2012

(87) PCT Pub. No.: WO2011/128639
PCT Pub. Date: Oct. 20, 2011

(65) Prior Publication Data
US 2013/0101655 A1    Apr. 25, 2013

(30) Foreign Application Priority Data

Apr. 12, 2010  (GB) .................................. 1006048.1
Dec. 3, 2010   (GB) .................................. 1020510.2

(51) Int. Cl.
| A01N 25/08 | (2006.01) |
| A01N 25/12 | (2006.01) |
| A01N 25/24 | (2006.01) |
| A01N 65/00 | (2009.01) |

(52) U.S. Cl.
CPC ............. *A01N 25/08* (2013.01); *A01N 25/12* (2013.01); *A01N 25/24* (2013.01); *A01N 65/00* (2013.01); *Y02A 50/322* (2018.01); *Y02A 50/325* (2018.01); *Y02A 50/326* (2018.01); *Y02A 50/328* (2018.01); *Y02A 50/329* (2018.01); *Y02A 50/33* (2018.01)

(58) Field of Classification Search
CPC ........ A01N 25/24; A01N 31/08; A01N 43/22; A01N 53/00; A01N 65/22; A01N 65/28; A01N 25/12; A01N 25/08; A01N 65/00
USPC ........... 424/409, 725; 514/28, 508, 531, 731
See application file for complete search history.

(56) References Cited

U.S. PATENT DOCUMENTS

| 4,590,062 A * | 5/1986 | Jang ............................. 424/469 |
| 6,221,375 B1 * | 4/2001 | Howse ................... A01N 25/26 424/405 |
| 7,803,832 B2 * | 9/2010 | Critcher et al. .............. 514/407 |
| 8,053,223 B2 * | 11/2011 | Meikle et al. ............. 435/254.1 |
| 2008/0118585 A1 * | 5/2008 | Nouvel .................. A01N 65/00 424/739 |
| 2010/0062944 A1 * | 3/2010 | Webster ................. A01N 25/34 504/358 |

FOREIGN PATENT DOCUMENTS

| DE | 19906491 A1 | 8/2000 | |
| DE | 10 2012 221 966 A1 | 6/2014 | |
| DE | 102012221966 A1 * | 6/2014 | .......... A01K 13/003 |
| GB | 2268676 * | 1/1994 | |
| GB | 2268676 A | 1/1994 | |
| GB | 2436288 A | 9/2007 | |
| JP | 2001151602 A | 6/2001 | |
| JP | 2009149579 A | 7/2009 | |
| WO | 02087342 A1 | 11/2002 | |
| WO | 2008062221 A2 | 5/2008 | |
| WO | WO 2008062221 A2 * | 5/2008 | |

OTHER PUBLICATIONS

International Search Report corresponding to International application No. PCT/GB2011/000572, dated Mar. 17, 2014.
Written Opinion of the International Searching Authority corresponding to International application No. PCT/GB2011/000572, filed Apr. 12, 2010.
Barton et al., Adhesive powder uptake and transfer by Mediterranean fruit flies, Ceratitis capitata (Dipt., Tephritidae). J. Appl. Entomol, Mar. 3, 2006, 130(5), pp. 257-262.
Meikle et al., "Impact of two treatments of a formulation of Beauveria bassiana (Deuteromycota: Hyphomycetes) conidia on Varroa mites (Acari: Varroidae) and on honeybee (Hymenoptera: Apidae) colony health" Exp. Appl. Acarol. (2008, 46(1-4), pp. 105-117.
Meikle et al., "Impact of a treatment of Beauveria bassiana (Deuteromycota: Hyphomycetes) on honeybee (*Apis mellifera*) colony health and on Varroa destructor mites (Acari: Varroidae)" Apidologie (2008) 39(2), pp. 247-259.
Nansen et al. "Uptake, retention and repellency of a potential carrier of active ingredients in crack and crevice treatments for stored-grain beetles" Journal of Stored Products Research, 2007, 43, pp. 417-424.

* cited by examiner

Primary Examiner — Carlos A Azpuru
Assistant Examiner — Courtney A Brown
(74) Attorney, Agent, or Firm — Sughrue Mion, PLLC

(57) ABSTRACT

A composite particle comprises i) an hydrophobic particle that adheres to the cuticle of one or more species of animal infesting arthropod; and ii) at least one organic chemical compound admixed therewith, wherein the said organic chemical is capable of controlling the population of at least one animal infesting arthropod species. Experiments proved the efficacy of the particle, for example in powder form, in relation to a variety of arthropods, for example red poultry mites.

1 Claim, 12 Drawing Sheets

CONTROL OF ARTHROPODS IN ANIMAL ENVIRONMENTS

CROSS REFERENCE TO RELATED APPLICATIONS

Figure 1:
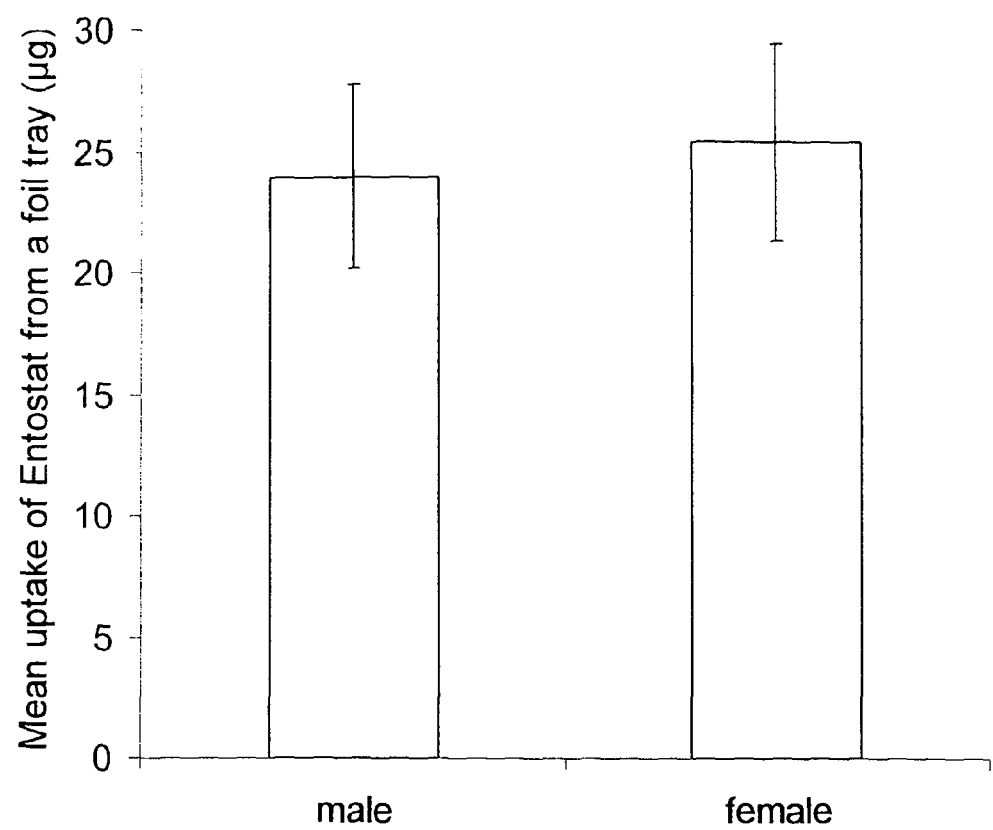

This application is a National Stage of International Application No. PCT/GB2011/000572 filed Apr. 12, 2011, claiming priority based on United Kingdom Patent Application Nos. 1006048.1, filed Apr. 12, 2010 and 1020510.2 filed Dec. 3, 2010, the contents of all of which are incorporated herein by reference in their entirety.

The present invention relates to methods of controlling arthropod infestation in animal environments and of arthropod infestation on animals, composite particles comprising chemical agents for controlling arthropod populations, compositions for treating arthropod infestations and uses thereof. In particular, the invention relates to methods comprising the application of dry powder formulations for controlling arthropod infestation in animal environments and in controlling arthropod infestation on animals, methods for the application of compositions in dry powder form to arthropods, dry powder compositions comprising organic chemical compounds in association with hydrophobic particles for controlling arthropod populations, methods of producing such compositions, dry powder composite particles, and uses thereof.

Synthetic organic chemicals have been used in the prior art in methods to control infestations of different kinds of arthropods in various settings. Examples of synthetic organic chemical groups that have been used in the past in controlling arthropod numbers in animal environments include the pyrethroids, such as α-cypermethrin, λ-cyhalothrin, and τ-fluvalinate, the organophosphates such as chlorpyriphos (diethoxy-sulfanylidene-(3,5,6-trichloropyridin-2-yl)oxy-1^{5}-phosphane), malathion (diethyl 2 dimethoxyphosphinothioyl-sulfanylbutanedioate), coumaphos (3-chloro-7-diethoxyphosphinothioyloxy-4-methyl-coumarin), and stirifos ([(E)-2-chloro-1-(2,4,5-trichlorophenyl)ethenyl]dimethyl phosphate) the carbamates such as amitraz (N-(2,4-dimethylphenyl)-N-[(2,4-dimethylphenyl) iminomethyl]-N-methylmethanimidamide), the spinosans such as spinosad (Dow Agrichemical, France), the GABA inhibitors such as fipronil (5-amino-1-[2,6-dichloro-4-trifluoromethyl)phenyl]-4 (trifluoromethylsulfinyl)pyrazole-3-carbonitrile), the neonicotinoids such as imidacloprid (N-[1-[(6-Chloro-3-pyridyl)methyl]-4,5-dihydroimidazol-2-yl] nitramide), the anthranilamides, the formononetins such as 7-Hydroxy-3-(4-methoxyphenyl) chromone, the essential oils such as tea tree oil, thyme oil (also known as thymol), and menthol, and the insect growth regulators such as methoxyfenozide (N-tert-butyl-N'-(3-methoxy-o-toluoyl)-3, 5-xylohydrazide);-(3-methoxy-2-methylbenzoyl)-3,5-dimethylbenzohydrazide) and the like. Chemicals for controlling arthropod numbers, such as those mentioned above, are often applied as sprays, dusts and/or as wash solutions to empty animal housings and their environs, such as sheds, kennels, stables, poultry sheds, pigsties and the like. In addition, chemicals for controlling arthropod numbers may be applied to the animal directly in the form of dips (e.g. sheep dip), sprays, washes, and baths. In such forms of application, there occurs considerable run-off of the chemicals into the environment. As one consequence of run-off, the environment suffers a chemical load which may deleteriously affect the immediate health of the animal to which it is applied. Furthermore, other non-domestic animals such as wild birds and amphibians may also suffer deleterious effects from run-off or the application of chemicals to the environment. Downstream consumers, including man, of animal products derived from treated animals may also suffer deleterious effects.

In conventional treatment methods as alluded to above, a significant disadvantage is that the concentrations of chemicals employed on application are relatively high so as to ensure a high degree of efficacy against the target arthropod(s). A further disadvantage of conventional treatment methods is that residual chemicals left in animal environments after treatment tend to degrade relatively rapidly and so repeat treatments have to be performed often.

When treating animals in baths, washes, dips and the like, the arthropod population controlling chemicals tend to remain on the animal coat for short periods of time. Indeed, should the animals be caught in the rain after such treatments, the chemicals are washed out of the animals coats and so the efficacy of treatment tends to be low.

There exists a need to overcome or at least reduce the drawbacks of conventional methods of treating animal housing areas and animals for arthropod infestation. These and other objects will become apparent from the following description and examples.

According to the present invention there is provided a dry powder composition that is effective in controlling at least one population of animal infesting arthropod species that comprises i) hydrophobic particles that adhere to the cuticle of the at least one animal infesting arthropod species; and ii) at least one organic chemical compound admixed with the said particles wherein the at least one organic chemical compound is one that is capable of controlling the at least one population of animal infesting arthropod species.

Naturally, the man skilled in the art will appreciate that by using dry powder compositions of the invention, such compositions may also be used for controlling arthropod infestation on animals as well as for controlling the arthropod population within an animal environment such as in animal housings and their environs, including sheds, cages, kennels, stables, poultry sheds, pig sties and the like. Accordingly, in an aspect of the invention there is provided use of a dry powder composition of the invention in the control of an arthropod population in an animal housing environment or its environs. In a further aspect of the invention there is provided use of a dry powder composition of the invention in the control of an arthropod population located on an animal.

The arthropod population to which dry powder compositions of the invention may be applied is any arthropod population, such as an ectoparasite arthropod population, that infests animals and/or their environs. The man skilled in the art will appreciate that included within the ambit of the term "arthropod" are all the stages of arthropod development that apply to any given arthropod species and may include the egg stage, larval stage, nymph stage, imago stage, and adult stage in an arthropod population, particularly an ectoparasite arthropod population. Such arthropod populations include but are not limited to dog fleas (*Ctenocephalides canis*), cat fleas (*Ctenocephalides felis*), pig (hog) lice, such as *Haematopinus suis*, mange mites, such as *Sarcoptes scabiei* var. *suis* (causing sarcoptic mange in pigs), follicular mites, such as *Demodex phylloides* (causing demodectic mange in pigs), ticks such as from *Boophilus* spp, *Amblyomma* spp. and *Ixodes* spp., such as *Ixodes ricinus* (sheep tick), *Ixodes hexagonus* (hedgehog tick), and *Ixodes canisuga* (British dog ticks), hard ticks e.g dog tick, brown dog tick, Gulf Coast tick, and rocky mountain wood tick, and soft ticks, such as the spinose ear tick (*O. turicata*), sticktight flea in pigs and poultry, *Dermanyssus* spp such as poultry red mite (*Dermanyssus gallinae*) affecting poultry, house flies from the *Musca* species (affect horses, pigs, humans, and cattle), such as *Musca domestica*, and face flies such as *Musca autumnalis, Drosophila* spp., *Calliphora* spp., such as the blue bottle, and *Stomoxys* spp., such as stable fly (*Stomoxys calcitrans*) (affects horses, cattle, pigs), mosquitoes such as *Anopheles* spp, *Culex* spp, and *Aedes* spp, horn flies such as *Haematobia irritans* (affect cattle and horses), horse flies, deer flies, black flies (also known as buffalo gnats), biting midgets (*Culicoides* spp.) (also known as "punkies" or "no-see-ums"), gnats and eye gnats such as *Hippelates* spp., common horse bot fly (*Gastrophilus intestinalis*), throat bot fly (*Gastrophilus nasalis*), nose horse bot fly (*Gastralis haemorrhoidalis*), and the like.

Without the intention of being bound by theory, it is thought that the particles that adhere to the arthropod cuticle do so via electrostatic forces maintained between the particles and the arthropod cuticle, such as an insect cuticle. Such particles maintain their electrostatic charge through the generation of electrical forces made by the rubbing of moving parts of the arthropod.

Typically, the hydrophobic particles of use in the invention carry the at least one organic chemical to the animal infesting arthropod cuticle placing it in contact therewith.

By making use of the electrostatic attraction of the carrier particles of use in the invention an efficient carrier system is achieved that is able to carry organic chemicals to target insect cuticle surfaces. By using particles of the invention, lesser amounts of chemical are required to effect control over the arthropod population, and thus there is less of a chemical load to the environment.

Dry powder compositions of the invention are capable of adhering to the fur, hair, feathers or skin of animals and as a result have a longer residence time on the animal than conventionally applied pesticidal treatments. As a consequence, the numbers of applications over time are lower, and the amount of chemical used over time is less. As a result of the longer residence time, the amount of chemical per unit volume of applied dry powder composition of the invention is also typically less than that required by conventionally applied compositions. A further advantage of dry powder compositions of the invention is that the chemical load to the environment is less than that for conventionally applied pesticidal treatments.

The dry powder compositions of the invention must be effective in controlling populations of animal infesting arthropods. The organic chemicals of use in the invention must be capable of acting on the at least one animal infesting arthropod species and once placed in contact with it, be capable of killing it or at least of rendering it dysfunctional with respect to its being able to eat and/or reproduce. Thus, dry powder compositions of the invention are capable of controlling populations of animal infesting arthropods, typically by reducing the population size.

Additionally, dry powder compositions of the invention may contain other components such as additives selected from UV blockers such as beta-carotene or p-aminobenzoic acid, colouring agents such as optical brighteners and commercially available colouring agents such as food colouring agents, plasticisers such as glycerine or soy oil, antimicrobials such as potassium sorbate, nitrates, nitrites, propylene oxide and the like, antioxidants such as vitamin E, butylated hydroxyl anisole (BHA), butylated hydroxytoluene (BHT), and other antioxidants that may be present, or mixtures thereof. The skilled artisan will appreciate that the selection of such commonly included additives will be made depending on end purpose, and perceived need.

Suitable organic chemicals of use in the present invention include those of conventionally applied organic chemicals that may be admixed within the hydrophobic particles of the invention and which do not deleteriously affect the ability of the chemical-loaded particle to adhere to the cuticle of the target arthropod or indeed, to the hair, skin, feathers or fur of a recipient animal. Examples of suitable organic chemical types of use in the invention may be selected from the pyrethroids, such as α-cypermethrin, λ-cyhalothrin, and τ-fluvalinate, the organophosphates such as chlorpyriphos (diethoxy-sulfanylidene-(3,5,6-trichloropyridin-2-yl)oxy-1^{5}-phosphane), malathion (diethyl 2 dimethoxyphosphino-thioyl-sulfanylbutanedioate), coumaphos (3-chloro-7-diethoxyphosphinothioyloxy-4-methylcoumarin), and stirifos ([(E)-2-chloro-1-(2,4,5-trichlorophenyl)ethenyl]dimethyl phosphate) the carbamates such as amitraz (N-(2,4-dimethylphenyl)-N-[(2,4-dimethylphenyl)iminomethyl]-N-methylmethanimidamide), the spinosans such as spinosad (Dow Agrichemical, France), the gamma amino butyric acid (GABA) inhibitors such as fipronil (5-amino-1-[2,6-dichloro-4-(trifluoromethyl)phenyl]-4 (trifluoromethylsulfinyl)pyrazole-3-carbonitrile), the neonicotinoids such as imidacloprid (N-[1-[(6-Chloro-3-pyridyl)methyl]-4,5-dihydroimidazol-2-yl]nitramide), the anthranilamides, the formononetins such as 7-Hydroxy-3-(4-methoxyphenyl) chromone, the essential oils such as tea tree oil, thyme oil (also known as thymol), citronella oil, and menthol, and the insect growth regulators such as methoxyfenozide (N-tert-butyl-N'-(3-methoxy-o-toluoyl)-3,5-xylohydrazide);-(3-methoxy-2-methylbenzoyl)-3,5-dimethylbenzohydrazide) and the like.

The organic chemical of use in the invention must be capable of controlling the population of arthropods, typically by significantly reducing the numbers thereof, such as by killing them. Suitable chemicals that may be admixed with hydrophobic particles of use in the invention include those chemicals as listed hereinabove.

The "at least one population of animal infesting arthropod species" refers to animal infesting arthropod species, such as from those listed hereinabove. The dry powder compositions of the invention can include more than one organic chemical that has the capacity of controlling the population of at least one animal infesting arthropod. Thus, compositions of the invention may be used to control 1, 2, 3, or 4 or more populations of arthropods, depending on the degree of infestation on the animal and/or in animal housing sites and the number of populations of species that are involved in the infestation. Thus a single composition of the invention may be loaded with two or more organic chemicals of choice depending on end purpose. Or, in the alternative, two or more compositions of the invention wherein each composition is loaded with one organic chemical of choice may be loosely admixed together forming a dry composition made up of two or more separate formulations of compositions of choice of the invention.

For the purposes of the present invention "controlling populations of animal infesting arthropod species" means that the arthropod population to which compositions of the invention are applied are ones that suffer a decrease in numbers due to death, ill health that may ultimately lead to death, and/or inability to reproduce or reduction in the ability to reproduce. Preferably, the controlling of populations of animal infesting arthropods means that at least 90% of the population of arthropods to which compositions of the invention are applied dies within 28 days of application of compositions of the invention. Preferably, the populations of arthropods that are adversely affected by compositions of the invention die or at best suffer sub-lethal effects which contribute to long-term population reduction as a result of the application of dry powder compositions of the invention to the animal and/or animal housing area. The man skilled in the art will appreciate that the population of animal housing arthropods to which the compositions of the invention are applied may be made up of one or more than one species of arthropod. Examples of species of arthropods that may make up a population of animal infesting arthropods that may be adversely affected by compositions of the invention include those arthropods as listed hereinbefore.

The hydrophobic particles of use in the invention are typically made up of waxes having a melting point of 50° C., more preferably of ≥60° C., and most preferably are made up of hard waxes having a melting point of ≥70° C. Suitable hydrophobic particles may be selected from waxes such as carnauba wax, beeswax, Chinese wax, shellac wax, spermaceti wax, candelilla wax, castor wax, ouricury wax, and rice bran wax. Such waxes typically display a high enthalpy of lattice energy during melt. Generally, the composite particles of use in the invention possess a volume mean diameter of ≥10 µm, such as ≥12 µm such as in the range of from ≥10 µm to 200 µm, for example from ≥10 µm to 100 µm; or from ≥10 µm to 40 µm; or from ≥10 µm to 30 µm or any desired volume mean diameter value thereinbetween. Preferably, dry powder compositions of the invention comprise composite particles having a volume mean diameter of ≥10 µm, for example of 10 µm, 11 µm, 12 µm, 13 µm, 14 µm, 15 µm and the like up to any volume mean diameter of choice, such as up to 200 µm or any volume mean diameter in between for example 40 µm or 30 µm. More preferably compositions of the invention comprise composite particles having a volume mean diameter of from about 12 µm to 200 µm. Such compositions are not considered to be a thoracic hazard and are not thought to be allergenic to humans.

Thus, as a further aspect of the invention, there is provided a composite particle for use in a dry powder composition of the invention that comprises i) an hydrophobic particle that adheres to the cuticle of one or more species of animal infesting arthropod; and ii) at least one organic chemical compound admixed therewith. Generally, the composite particles of use in a dry powder composition of the invention possess a volume mean diameter as defined herein. To obtain particles of a volume mean diameter of use in the invention, hydrophobic materials in the form of, for example, 1 to 5 kilogram blocks or tablets may be broken up or kibbled into small millimeter-sized pieces (such as from 2 mm-8 mm approximate diameter in size, for example from 4 mm to 6 mm) in a kibbling machine. The millimeter-sized pieces are then passed through a comminuting means such as a standard mill, e.g. an Apex Comminuting mill, and milled or comminuted into particles having an approximate diameter in the range from 100 µm-500 µm, for example from 250 µm-300 µm. The micron-sized comminuted particles are then passed through a micronising apparatus, such as an AFG micronising air mill to obtain particles of a desired VMD range, such as from 15 µm-20 µm, that is of use in the present invention. The skilled addressee will appreciate that such procedures for obtaining small particles are well known in the art. Preferably, dry powder compositions of the invention comprise composite particles having a volume mean diameter of ≥10 µm, for example of 10 µm, 11 µm, 12 µm, 13 µm, 14 µm, 15 µm up to 40 µm or any value thereinbetween. As stated herein, the volume mean diameter of the composite particles typically lies in the range from 10 µm to 200 µm, and more preferably is from 12 µm to 200 µm and may have a value that lies anywhere thereinbetween.

Compositions of the invention wherein at least 50% by volume of particles is ≥12 µm are not thought to be a thoracic respiration hazard to humans because at such sizes they are considered too large to be inhalable. Furthermore, by using compositions of the invention, a targeted means of delivering lower amounts of chemicals to target populations of arthropods more efficiently than in prior art methods is achieved.

In a further aspect of the invention there is provided a method of producing dry powder compositions of the invention comprising the steps of
i) admixing at least one chemical organic compound that is capable of controlling the population of an animal infesting arthropod species with a liquid hydrophobic carrier substance;
ii) allowing the admixture of the liquid hydrophobic carrier substance and the at least one chemical compound of step i) to cool to a solid state; and
iii) milling and/or micronising the admixture forming a dry powder.

Typically, the dry powder is made up of micronized composite particles of a volume mean diameter as herein described, for example of about 10 µm, preferably of a volume mean diameter of about 12 µm.

To obtain particles of a volume mean diameter of use in the invention, the cooled solid hydrophobic carrier substance in the form of, for example, 1 to 5 kilogram blocks or tablets may be broken down or kibbled into small millimeter-sized pieces (such as from 2-8 mm in approximate diameter in size, for example from 4 to 6 mm) in a kibbling machine. The millimeter-sized pieces are then passed through a comminuting means such as a standard mill, e.g. an Apex Comminuting mill, and milled or comminuted into particles having an approximate diameter in the range from 100 µm-500 µm, for example from 250 µm-300 µm. The micron-sized comminuted particles are then passed through a micronising apparatus, such as an AFG micronising air mill to obtain particles of a desired VMD size range as outlined herein, such as from 15 µm-20 µm, that is of use in the present invention. The skilled addressee will appreciate that such procedures for obtaining small particles are well known in the art.

In a further aspect of the invention there is provided a method of controlling the population of an animal infesting arthropod species in an animal housing area wherein composite particles according to the invention are presented to the surfaces of an animal housing area by
i) collecting the composite particles in a dusting apparatus;
ii) releasing the said particles from the said dusting apparatus and into the said animal housing area.

In a further aspect of the invention there is provided a method of controlling the population of an animal infesting arthropod species on an animal wherein composite particles according to the invention are presented to the surfaces of the animal by
i) collecting the composite particles in a dusting apparatus;
ii) releasing the said particles from the said dusting apparatus and onto the surface of an animal.

Furthermore, depending on the manner in which the dry powder compositions of the invention may be applied to animals, particularly to birds, compositions of the invention may be supplied as an additive to receptacles such as trays, sand boxes, and troughs that contain sand or dirt, or simply to certain areas of ground, such as to depressions in the earth and the like which the animal or bird uses for dust bathing. Such receptacles or areas of ground may contain fine sand or 'ground dirt' (dust) that may be further supplemented with dry powder compositions of the invention so that the dust-bathing behaviour of the animal or bird is employed to coat itself with compositions of the invention. Such receptacles comprising sand or dry 'ground dirt' (dust) laced with dry compositions of the invention have particular use for farm-yard birds that may indulge in dust bathing such as free range hens and game birds bred in captivity such as pheasants, partridges, guinea fowl, peacocks and the like.

The skilled artisan will appreciate that the animal can be selected from domestic pets, including canine animals such as a dog, a bitch or a puppy, feline animals such as a tom, a queen, or a kitten, and from livestock including equine animals such as a horse e.g. a gelding, a mare, a foal, a filly, or a stallion, bovine animals such as a bull, a cow, an heifer, a steer, or a calf, ovine animals such as a ram, an ewe, or a lamb, and porcine animals such as a sow, a boar, barrow, stag, gilt or a piglet.

There now follow examples and figures illustrating the invention. It is to be understood that the teaching of the examples and figures is not to be construed as limiting the invention in any way.

FIGURES

FIG. 1: Mean uptake of Entostat® powder (carnauba wax powder) from inert foil surface by male and female *C. capitata*

FIG. 2: Percent of female *C. capitata* moribund at each time point after treatment on Entostat® (carnauba wax powder) containing different concentrations of Spinosad FIG. 3: Percent of male *C. capitata* moribund at each time point after treatment on Entostat® (carnauba wax powder) containing different concentrations of Spinosad FIG. 4: Proportion of *C. capitata* flies in each category (mating, mated male knocked down, mated female knocked down, unmated female knocked down) at different time periods after treated males (treated on 2% spinosad in Entostat) were introduced to a population of untreated females FIG. 5: Free range Poultry shed. Key: Numbered squares (□) indicate the location of mite traps under slats.

FIG. 6: Mean retention of carnauba wax powder (μg) per individual mite at each time interval post treatment. An exponential curve has been fitted to the data.

FIG. 7: Mean amounts of Carnauba wax powder in swab samples at each time interval post treatment of caged hens FIG. 8: Mean amounts of Carnauba wax powder in swab samples at each time interval post treatment of free range hens FIG. 9: Mean amounts of Carnauba wax powder in swab samples at each time interval post treatment of dairy cattle FIG. 10: Mean amounts of Carnauba wax powder in swab samples at each time interval post treatment of sheep FIG. 11: The proportions of initial powder uptake lost by each time point after treatment by each animal type FIG. 12: Mean amount of carnauba wax powder detected on rectal, chest and under wing at different times post application

EXAMPLES SECTION

Feasibility Project Objectives

The aim of this study was to formulate carnauba wax (in the form of Entostat® powder owned by Exosect Ltd) with natural essential oils that act as an environmentally positive miticide against *Dermanyssus gallinae* (red mite).

Key issues to be addressed:

- Phase 1: What percentage of active ingredient (AI) is required to kill *Dermanyssus gallinae* (red mite) efficiently, whilst not harming poultry?
- Phase 2: How should Entostat® be formulated to maintain the important electrostatic features of the powder and remove the need for potentially hazardous chemical solvents?

The technical feasibility of a cost-effective alternative to existing synthetic chemical treatments of mite control for organic farming is provided here.

Phase 1—Assessment of Essential Oils

Active ingredients tested are thymol and tea tree oil.

Phase 2—Selection of Appropriate Essential Oil Concentration Dosage of Formulation Agent A series of experiments was completed to determine how and in what quantities thymol and tea tree oil can be infused into Entostat® without disrupting the sensitive electrostatic properties. The major points of investigation were:

- Solvent selection—acetone and ethanol
- Ratio required of solvent to active ingredient.
- Effect of solvent on powder drying
- Effect of formulation on electrostatics (Faraday cup experiments)

Results are highlighted in Table 1 (below).

TABLE 1

Preliminary results of ExoMite ® Powder formulation

| Solvent | Electrostatic Charge | Comments |
|---|---|---|
| Acetone | ++ | Dry powder after 24-h<br>Powder friable |
| Ethanol | +++ | Powder dry after 72-h<br>Powder friable |

In summary, the results from table 1 indicate that acetone and ethanol may be used to formulate active ingredient into the electrostatic powder (Entostat®). The electrostatic properties are not disrupted whilst the powder is dry and friable within 24 and 48 hours of formulation in the acetone and ethanol treatments, respectively.

Table 2 summarises the results from loading the powder with an active ingredient to examine the effect on electrostatic performance.

TABLE 2

| Active Ingredient | Solvent | A.I. % | Friability/Charge |
|---|---|---|---|
| Thymol | Acetone | 1 | Good, + |
| | | 2.5 | Good, + |
| | | 5 | Good, + |
| | | 7.5 | Good, + |
| | | 10 | Good, + |
| | Ethanol | 1 | Good, + |
| | | 2.5 | Good, + |
| | | 5 | Good, + |
| | | 7.5 | Good, + |
| | | 10 | Good, + |
| Tea-tree | Acetone | 1 | Good, + |
| | | 2.5 | Good, + |
| | | 5 | Good, + |
| | | 7.5 | Good, + |
| | | 10 | Good, + |

TABLE 2-continued

| Active Ingredient | Solvent | A.I. % | Friability/Charge |
|---|---|---|---|
| | Ethanol | 1 | Good, + |
| | | 2.5 | Good, + |
| | | 5 | Good, + |
| | | 7.5 | Good, + |
| | | 10 | Good, + |

In summary, Table 2 shows that no detrimental effects were noted when formulating the powder at up to 10% active ingredient with acetone or ethanol.

Poultry Rearing Environment

Exosect investigated the use of combining Entostat powder with a pyrethroid as a control measure for animal health pests.

Initial market investigation showed there was a market for the control of red poultry mite *Dermanyssus gallinae* in poultry rearing centres.

Studies have confirmed over 85% of UK poultry houses are infested with this pest.

Due to the nature of the poultry industry for both egg and meat production it was deemed appropriate to treat the fabric of the poultry buildings rather than the birds themselves. This therefore would require an initial pre-application of product in the form of a crack and crevice treatment and later top ups with a similar system when the birds were out of the housing.

Active Ingredient (ai) Selection

The selection of an ai was done on the basis that the ai:
  was active against the particular pest
  was representative of a class of active ingredients suitable for use in the field.
  has a reasonable profile with regard to human toxicology.
  A synthetic pyrethroid, alpha-cypermethrin (available from a range of agrochemical companies, e.g. BASF) was selected as the ai for the trial.

ai—alpha-cypermethrin formulation—0.5% in Entostat® powder and applied as a dust.

Trial Location

The trial was performed on a poultry shed on a free range egg production farm with a known history of infestation with the pest and achieving poor control of the pest using synthetic pyrethroids applied as a wash. The site was Portland Poultry Farm, near Basingstoke, Hampshire.

Treatment

The treatment was applied as a crack and crevice treatment. When not resident on the body of the birds the mites hide in cracks and crevices within the fabric of the poultry house. The formulated Entostat powder was deposited in the cracks and crevices using a battery powered dusting machine (Supplier: Gremar Inc., Iowa, USA). This would ensure the powder was forced into the cracks and crevices.

Trial Design

Figure 5:
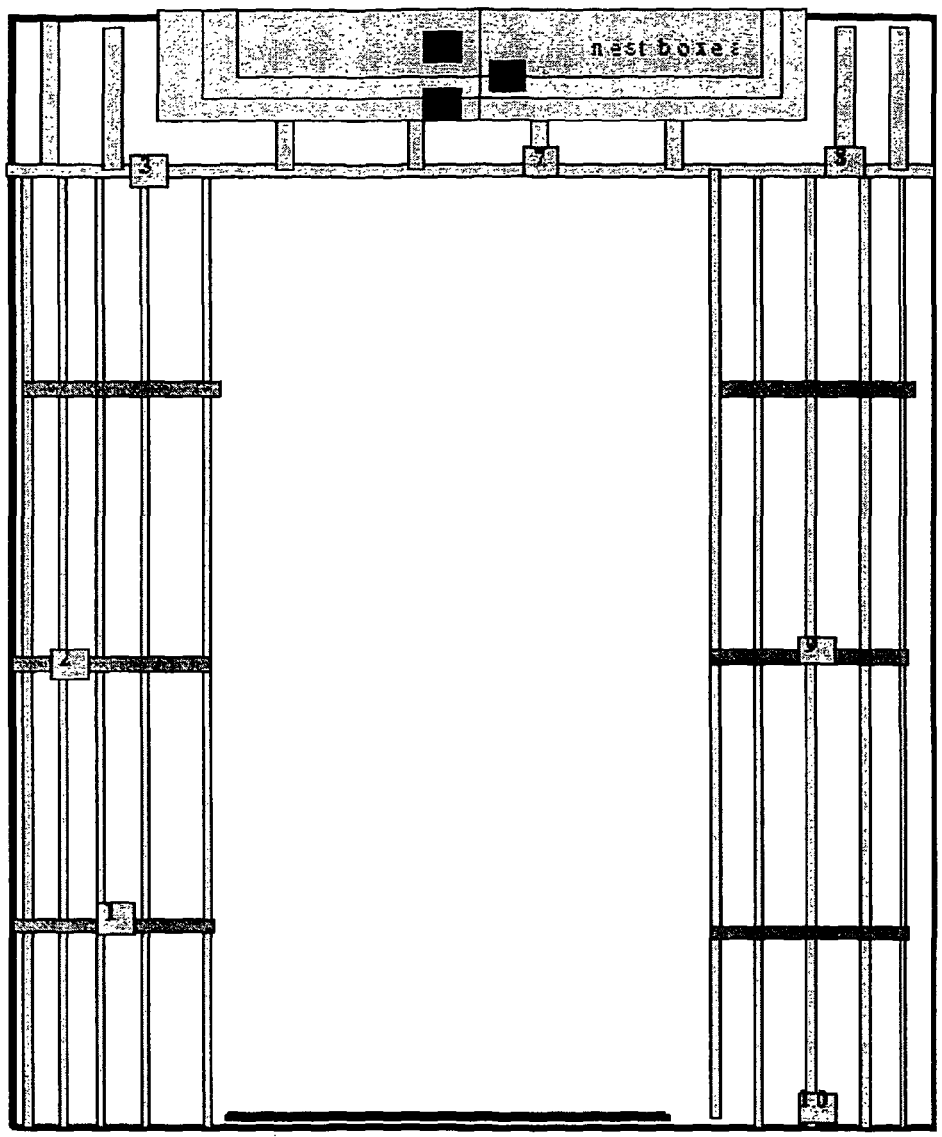

The pest was monitored with the use of standard monitoring traps placed as per the diagram (FIG. 5). The purpose of monitoring was to quantify the pest population prior to the establishment of the trial and to judge the efficacy of the treatment after the application.

The trial layout is shown in FIG. 5.

Results

Counts were classified as
1. Very high—>500
2. High—200-500
3. Moderate—50-200
4. Low—<50
5. Uninfested—0

TABLE 3

| Sample Site | 30 Days Prior to Treatment (DPT) | 0 Days After Treatment (DAT) | 11 Days After Treatment (DAT) Adults | 11 Days After Treatment (DAT) Nymphs |
|---|---|---|---|---|
| 1 | >500 | >500 | <50 | 200-500 |
| 2 | >500 | >500 | 0 | 200-500 |
| 3 | >500 | >500 | 0 | 200-500 |
| 7 | <50 | 50-200 | 0 | 0 |
| 9 | >500 | 50-200 | 0 | 0 |
| 10 | >500 | <50 | 0 | 0 |

Discussion

The results demonstrated that there were 2 relatively uniform sub plots within the treated area and consisted of a high infestation area (sample sites 1-3) and a moderate treatment area (sample sites 7-10) of the target pest in the trial site and that the pest was present for at least one month prior to the application of the treatment. The treatment achieved a consistent and even pest knockdown of pests present during the treatment and displayed sufficient residual in the moderate infestation to control nymphs hatching from eggs after the treatment. The treatment was deemed effective as a single application treatment for low to moderate infestations.

*C. capitata* (Mealy) Mortality Bioassays—Summary

Medflies were treated by dropping them onto a thin layer of Entostat coated onto an inert foil surface. This method simulated uptake from a dispenser, and ensured only a small and consistent quantity of powder was taken up. Entostat was dyed with a fluorescent marker in order to quantify how much powder was taken up by medflies when contacting the surface. Entostat-treated medflies could then be washed in solvent and the solvent sample measured for the amount of fluorescence given off using a fluorometer (FIG. 1). This enabled us to determine the quantities of powder/active on treated flies at each insecticide concentration (Table 4).

Methodology for the Entostat Bioassay:
  Five concentrations of Spinosad in Entostat were prepared for the experiment using methods commonly employed in the art, along with a vehicle control of blank Entostat:
  0% (control)
  0.05%
  0.1%
  0.5%
  1%
  2%
  Flies were dosed by dropping them onto a foil container coated in a thin layer of formulated powder, then allowing them to fly away before being captured in and individually housed in a small pot.
  Ten male flies and ten female flies were tested at each concentration, and there were also ten each that were not treated with anything (negative control).
  Individual flies were dosed inside an upturned fly cage. A foil container was dusted with formulated Entostat. Excess powder was tapped off and the foil was placed on the bench, inside the fly cage. An individual fly was captured in a vial, the vial was upturned above the foil, the vial was tapped so that the fly dropped out and onto the foil. If the fly flew away, this fly was captured in a housing pot containing a drinker and a small quantity of dry diet and included in the experiment.

The flies were checked at regular intervals. A record was made of whether they were dead, alive or moribund.

Probit analysis was run on the entire dose response data to calculate the KT50 and KT90 for each dose of spinosad. In all tests males were killed more rapidly than female flies. KT50 and KT90 refer to time until 50 or 90% of the flies are 'knocked down' (moribund) respectively.

Figure 2:
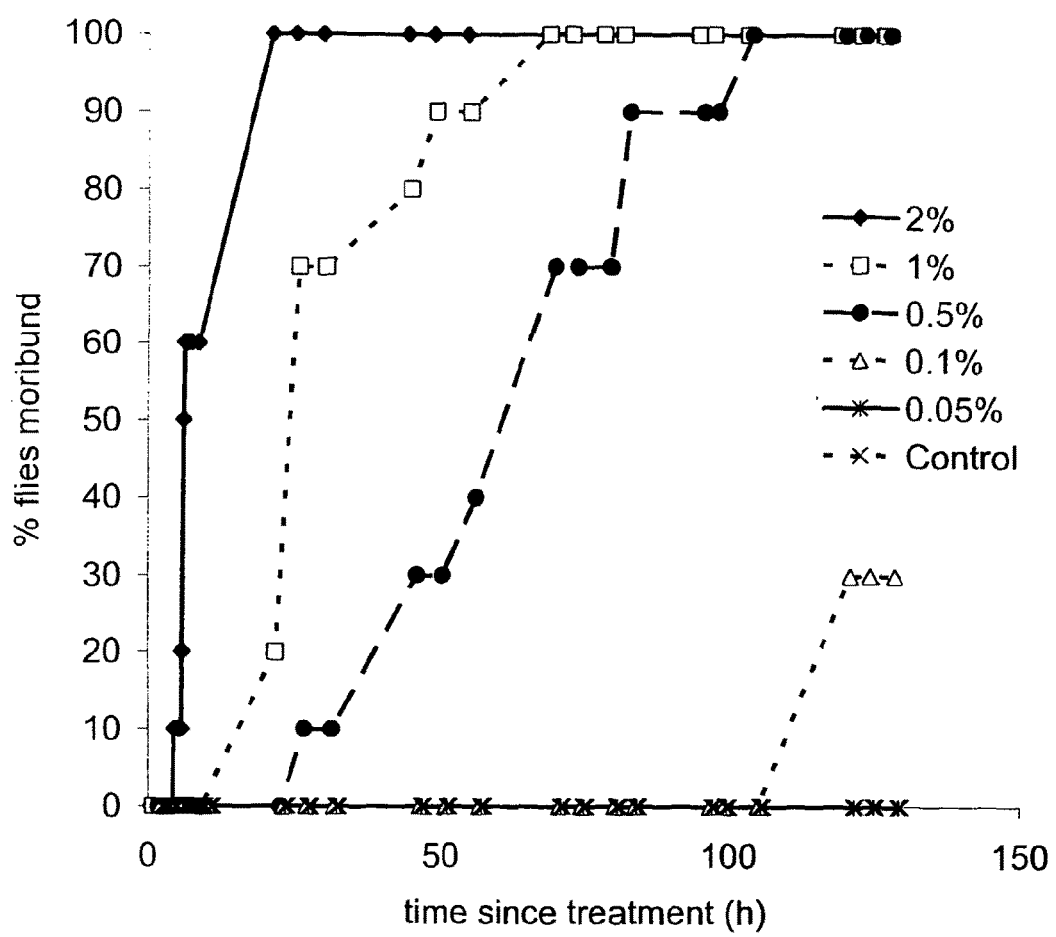
Figure 3:
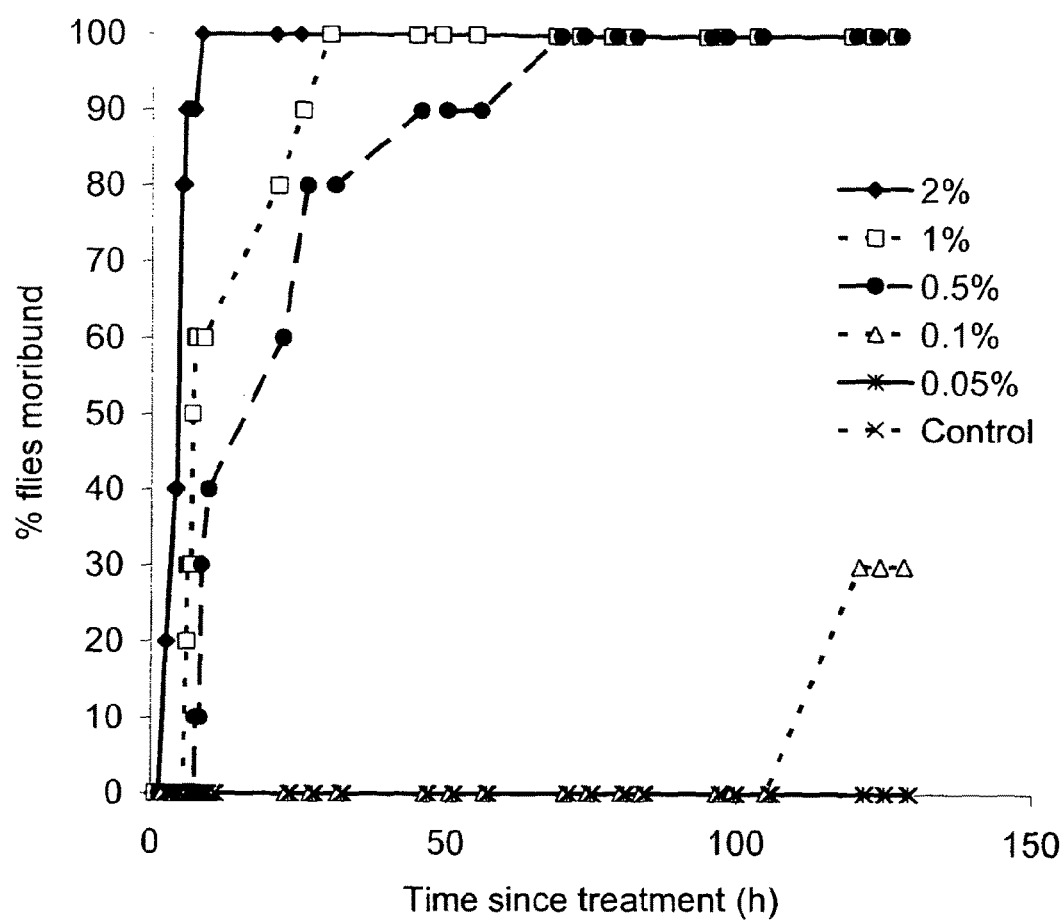

Spinosad in Entostat proved efficacious when spinosad was >0.5% w/w. Lower doses did not cause significant mortality compared to controls. Entostat extended the LT50 to 21 and 61 h for males and females respectively at the lower dose of 0.5%, whilst causing 50% knockdown to males and females at 6 and 4 h respectively at 2% (FIGS. 2 and 3). Thus Entostat appeared to result in a slow release of spinosad, which is consistent with formulation methods; this may be useful for allowing time for secondary transfer of active ingredients to conspecifics.

Spinosad in Entostat at a dose of 2% w/w was used for further studies on secondary transfer to conspecifics. In replicated bioassays, treated males were released with untreated virgins of the opposite sex in arenas. Mating couples were isolated, alongside an unmated individual and each was observed for knockdown over time:

- 27 four-six day-old virgin male medflies were treated with 2% spinosad Entostat powder by dropping them on a foil tray coated in a thin layer of powder. They were housed in a tank containing at least 100 four-six day-old virgin female flies.
- The holding tank was observed and when a copulating pair was observed, the mating pair was removed and transferred to a separate pot.
- On removal of the mating pair, an unmated female was selected randomly from the same tank and also individually housed.
- The mating pairs that were observed were then separated and placed into separate pots—the female into a clean pot. Any knockdown or death was recorded including the sex and time of knock down (the flies being in a moribund state) and death. The cage was also observed and any moribund flies and death of flies was recorded. When a fly was noted as moribund it was removed from the tank.
- At the end of the day, food and water was provided to the remaining survivors in the pots. Survival was monitored for up to 3 days after treatment.

Figure 4:
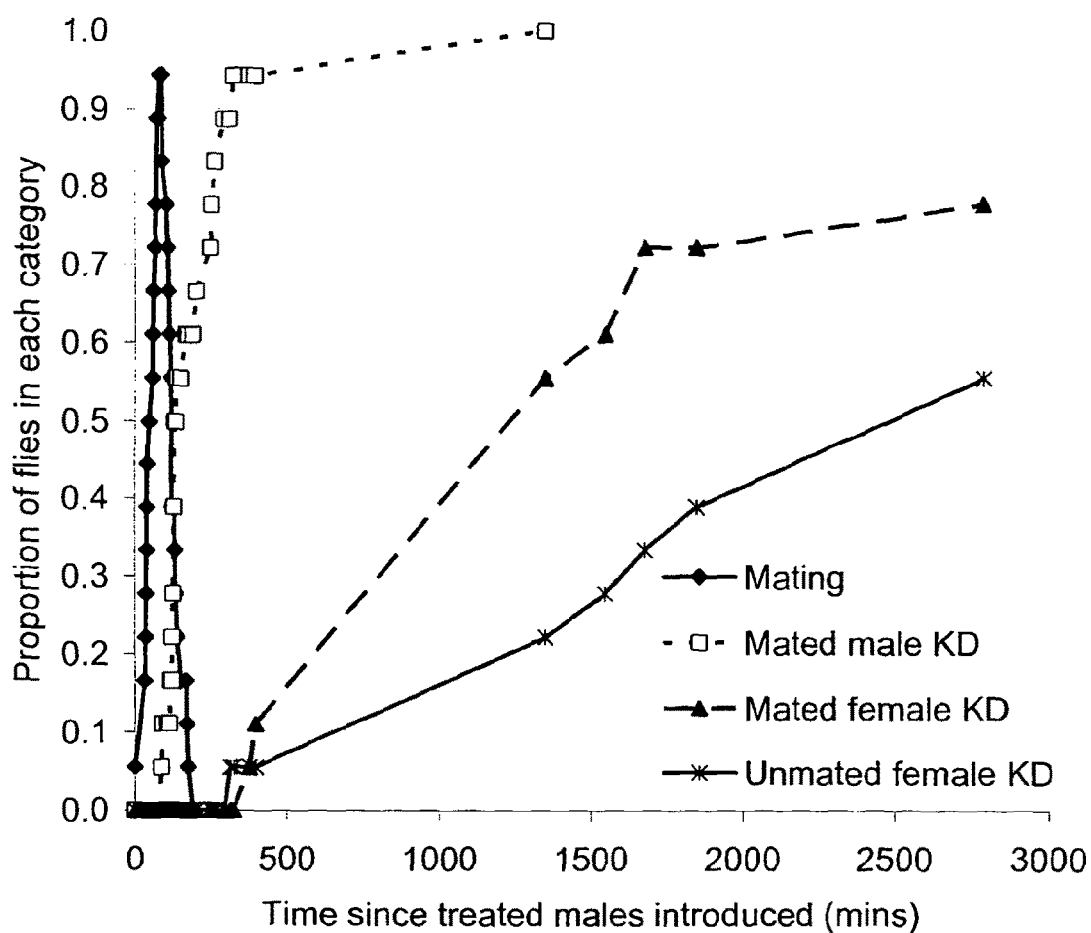

Untreated females were knocked down at a faster rate after mating with a treated male than those which did not mate (FIG. 4).

TABLE 4

Amount of spinosad on fly (μg) at each concentration:

| Spinosad concentration in Entostat % | Male | Female |
|---|---|---|
| 0.05 | 0.012 | 0.013 |
| 0.1 | 0.024 | 0.245 |
| 0.5 | 0.12 | 0.13 |
| 1 | 0.24 | 0.26 |
| 2 | 0.48 | 0.51 |

Uptake of Powder By Red Poultry Mites

1. Objectives

To examine the potential of carnauba wax powder as the carrier of an active principal for control of red poultry mite (*Dermanyssus gallinae*) by examining its ability to adhere to the target pest.

2. Study Outline

The ability of carnauba wax powder to adhere to the mites after a 'puffer-type' application was assessed. The persistence of the carnauba wax powder on mites over time was examined.

3. Test Item Details 2 kg carnauba wax blocks are first kibbled into approximately 4 to 6 mm pieces in a KT Handling Ltd Model 04 kibbler following the manufacturer's instructions. The kibbled pieces are then passed through an Apex Construction Ltd Model 314.2 Comminuting Mill and reduced further in size to a range of 250 to 300 um. The comminuted particles are then passed through a Hosokawa Micron Ltd Alpine 100AFG jet mill following the manufacturer's instructions, setting the mill at a speed of 8000 rpm, with a positive system pressure of 0.03 bar. The grinding air is held at 6 bar, the system rinsing air flow and Classifying Wheel gap rinsing air are both set at a minimum of 0.5 bar and no more than 0.75 bar in order to achieve a final population of particles with a VMD of about 16 um.

Carnauba wax powder was formulated with the fluorescent dye 7-Diethlyamino-4-methylcoumarin at 5% (w/w).

4. Test System

Mites (of mixed age and gender) were obtained from a Somerset poultry farm (caged hen egg production) and brought to Exosect for treatment. Mites were separated into groups and then left overnight to acclimatise before treatment.

5. Test Location

Tests were conducted in an insectary bioassay room. The laboratory was set to 22° C.

6. Experimental Design

Mites were treated and analysed in groups of ten. Five batches of five groups were each treated and then one batch analysed after each time point (0, 1, 2, 6 or 24 h).

For treatment mites were each transferred using a paint brush into 9.5 cm Petri dishes which were then sealed using parafilm. Mites were chilled for ease of handling. After 24 h each dish was opened, placed on the bench 20 cm in front of the duster and puffed five times with dyed carnauba wax powder. In the 0 h treatment each mite was then lifted using a paintbrush and deposited into a 1.5 ml Eppendorf tube, one group of ten per tube. For the other treatments (1, 2, 6 and 24 h) each mite was transferred to a clean Petri dish, one group per dish. Each group were then transferred to an Eppendorf tube after the appropriate time interval had elapsed. Once mites had been collected the tubes were labelled and frozen for fluorometric analysis.

7. Application Details and Regime

The duster was held at approx 45° at the bench and 20 cm away from the dish to be treated. This optimum position of the Petri dishes to receive the puff of powder was previously established by trial and error application and marked.

Before application to mites, the variance in the dispatch of powder by the duster was assessed by puffing 10 Petri dishes with dyed carnauba wax powder, one after the other, and weighing them. Each dish received a mean quantity of carnauba wax powder of 9.21 g±1.16 (SE) with one puff.

During application each Petri dish to be treated was placed in the marked position and puffed five times. After ten seconds the dish was moved and the mites removed by paintbrush.

8. Sampling/Measurement Regime

Quantification of powder on each group of mites was made using fluorimetry following methods as outlined hereinbefore.

Statistical Analysis

Powder decay on mites was analysed using regression analysis and by fitting of an exponential curve to the relationship. To improve the fit the 6 h data were removed from the plot. The half life (t) of powder retention was calculated using the equation: $=\ln(2)/k$ where k is the rate constant (the value is identified in the equation of the slope) and $\ln(2)$ is the natural logarithm of two.

9. Results

Figure 6:
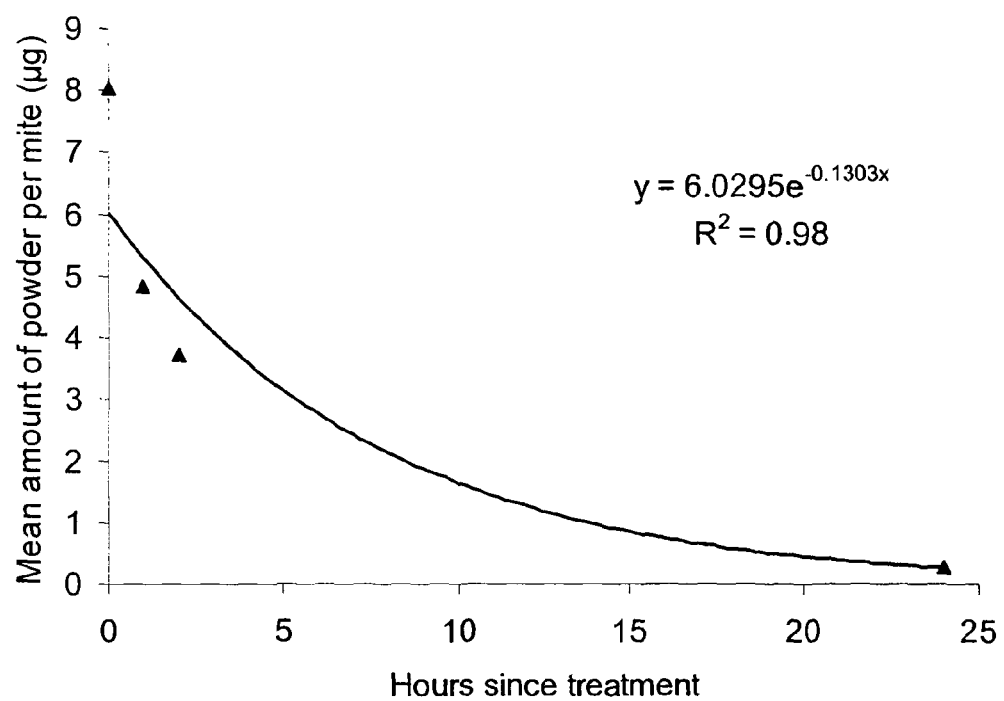
Figure 7:
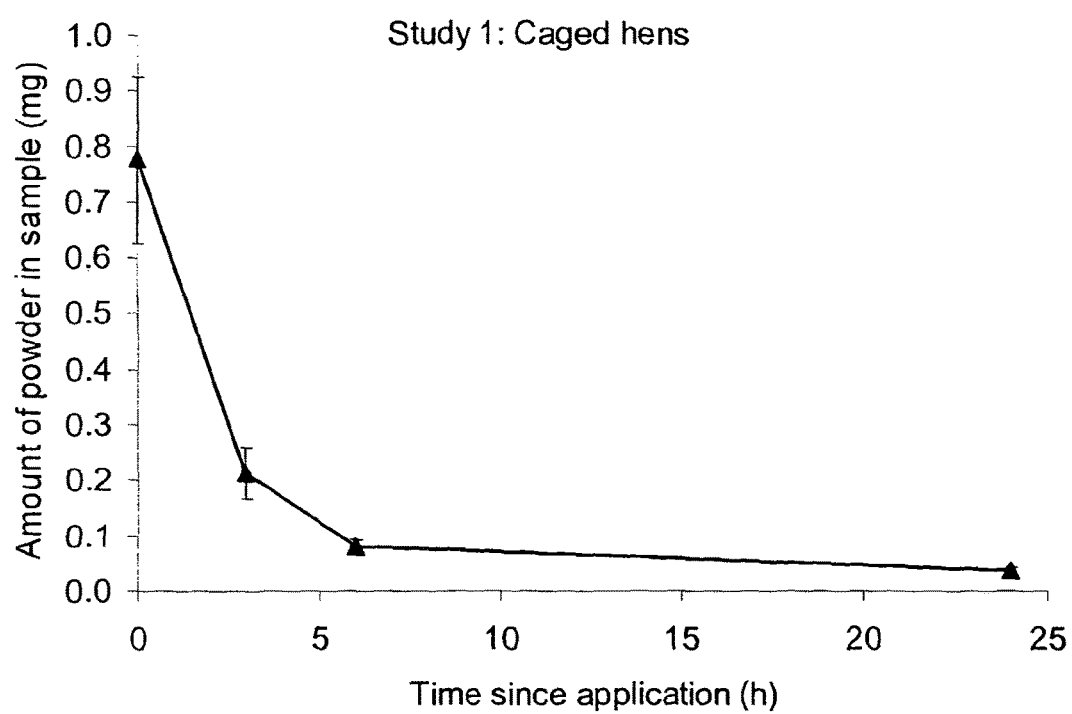
Figure 8:
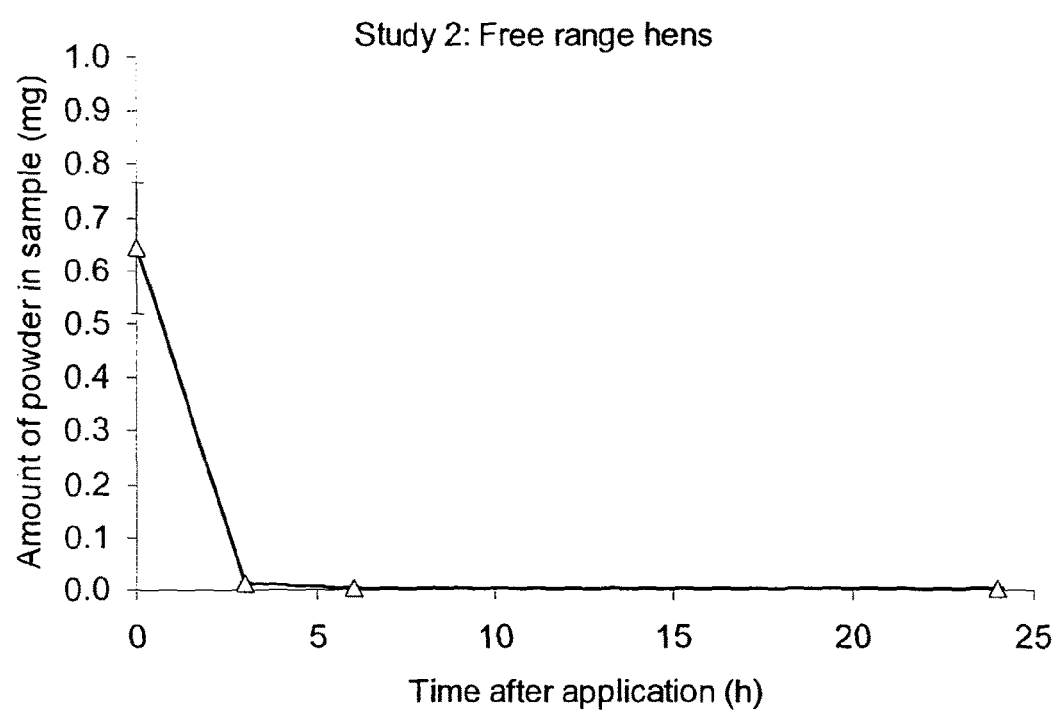
Figure 9:
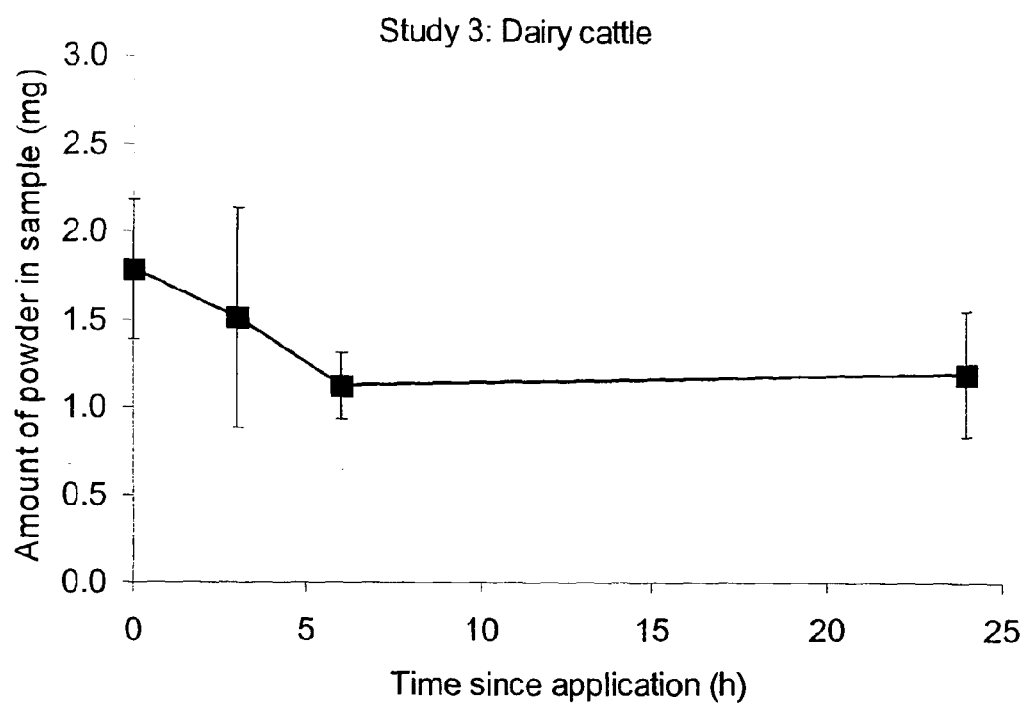
Figure 10:
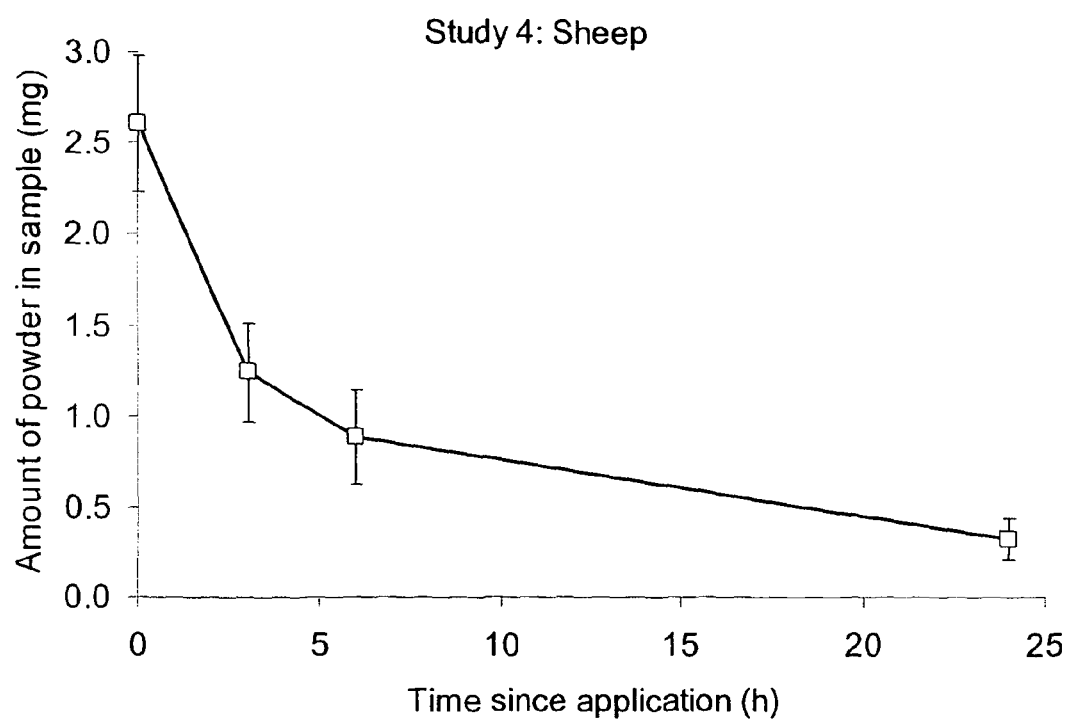

Carnauba wax powder could be detected on mites at all time points post treatment. Quantities at 6 h post treatment were lower than expected, possibly due to extra handling of the mites that was required after treatment. In some of these replicates the integrity of the parafilm failed and the mites had to be moved back inside the dishes and resealed. Extra handling of the mites post treatment could have caused additional loss of powder to the paintbrush. A few mites escaped and the calculated mean amounts of powder were adjusted accordingly. An exponential curve was fitted to the data (mean amount of powder per mite) with and without the inclusion of the 6 h time point and the fit of the data was much improved by removing the 6 h data. The mean retention of powder per group of mites is shown in Table 5 and FIG. 6 shows the exponential fit to the mean amounts of powder per mite at each time interval without the 6 h time point. With an $R^2$ value of 0.98 the data show a very close fit to an exponential relationship and from this a half life of powder loss from mites was calculated at 5.32 h. Therefore after every 5.32 h interval half the powder attached to the cuticle is lost.

TABLE 5

Mean retention of powder per group of mites at each time interval since treatment

| Time since treatment | Mean powder per group of mites (µg) | Standard Error |
|---|---|---|
| 0 h | 80.26 | 7.77 |
| 1 h | 48.34 | 3.98 |
| 2 h | 34.43 | 3.74 |
| 6 h | 2.61 | 0.23 |
| 24 h | 2.65 | 0.41 |

10. Summary

The studies showed that carnauba wax powder would adhere to *Dermanyssus gallinae* after a puffer type application and that the powder would be retained on the cuticle >24 h. Powder was lost from the cuticle at an exponential rate with a half life of 5.32 h.

Uptake of Powder by Domesticated Animals

1. Objective

A study to examine the potential of carnauba wax powder as the carrier of an active principal for the control of domesticated animal arthropod disease vectors and/or parasites. In this study the uptake and retention of powder was quantified on a variety of animals: chickens (free range and caged egg-laying stock), sheep and dairy cattle.

2. Study Outline

The ability of carnauba wax powder to adhere to each domesticated animal after a 'puffer-type' application was assessed. Furthermore the persistence of the powder on the animal coats and feathers over time was examined up to 24 h after treatment. Applications of fluorescently labeled powder were made to discrete 10 $cm^2$ areas on the animals and swabs of the areas were collected at set time points to quantify the amount of powder remaining. Four animal groups were tested:

Study 1: Uptake and retention of powder on caged hens

Study 2: Uptake and retention of powder on free range hens

Study 3: Uptake and retention of powder on cattle

Study 4: Uptake and retention of powder on sheep

An additional test was carried out on caged hens whereby two hens were dusted at three different sites (under wing, breast bone, rectal area) and swabs taken from each. The purpose of this test was to ascertain whether it was practical to apply powder to the whole hen (in caged hens this might be the most practical way to treat them) and whether it would demonstrate differing adherence properties in each area.

3. Test Item Details

Carnauba wax powder was formulated with the fluorescent dye 7-Diethlyamino-4-methylcoumarin at 5% (w/w) following methods as outlined hereinbefore.

4. Test System

Hens, sheep and cattle for testing were selected from co-operating farms in Somerset. Individual cattle and sheep were tracked through the studies by means of the farmers tagging system; however tracking by cage was only possible for the caged birds and was not possible at all for the free range hens.

Patch testing was conducted on each animal type (on different individuals to those used in the main tests) in the week prior to experimentation by selecting at least three animals and swabbing a small 1 $cm^2$ patch of skin with a small quantity of dyed carnauba wax powder on a Q tip (cotton bud). Each patch was checked approximately 1, 3 and 24 h after the patch test to check that no reaction to the treatment had occurred (i.e. red, itchy or swollen skin). However since the powder is made of food grade carnauba wax and a very low concentration of the fluorescent dye, no reactions were expected.

Sheep and cattle test animals were kept indoors throughout the 24 h test period and so were not exposed to unsettled weather. Free range birds were allowed to roam outside and dust bathe under their normal conditions immediately after the initial post application sample was taken and again after the 3 and 6 h sampling periods. The weather was dry and bright throughout. Free range birds were brought indoors overnight, between the 6 and 24 h sampling points.

5. Experimental Design

Ten replicate animals were randomly selected for each animal group and identified as A-J subjects (except hens). Each animal received five puffs of dyed carnauba wax powder from a duster apparatus onto a selected area of the body (approx 10 by 10 cm area). For sheep and cattle this was on the top of the shoulders. For poultry this was under the wing. Free range hens were marked with a purple dye on the back of the neck to ensure that the same group of birds was selected at each time point. A card template with a 3 cm by 3 cm window was held up against the top left hand side of the treated area and the entire area of the window was swabbed with a moistened (distilled water) Q tip (trimmed to 2 cm length). Each Q tip was placed into an individual 1.5 ml Eppendorf tube and labeled before transport back to the lab. A fresh template was used for each animal. Additional swab samples were taken from the animals at the following time points:

3 h: top right hand side of treated area
6 h: bottom left hand side of treated area
24 h: bottom right hand side of treated area In the minor test where whole hens were treated, two caged hens were selected, held upside down by their legs and rotated while repeat applications of dyed carnauba wax powder were made to the different body parts. At 0, 3, 6 and 24 h swabs of a 3 cm² area were taken from the rectal, breast and under wing areas.

6. Sampling/Measurement

Quantification of powder on each animal swab was made using fluorimetry Determination of Entostat Content with Fluorimetry following methods as outlined hereinbefore.

7. Statistical Analysis

Powder loss on animals did not follow exponential decay curves so linear regression analysis was not used to compare rates of loss between animal groups. Instead the proportion of powder lost by each animal between 0-3 h and 0-24 h was calculated (for hens the amount lost at 3 and 24 h was deducted from the mean initial uptake at 0 h because individual hens could not be tracked). The proportions of powder lost between groups were compared using Kruskal Wallis tests followed by pair-wise comparisons using the Dunn's procedure with a Bonferroni adjustment.

The initial uptake of powder was compared between animal groups using one way ANOVA. The data were first square root transformed to normalise them. Pair-wise comparisons between groups were made using Tukeys HSD test.

8. Results 8.1 Patch Testing

Hens, cattle and sheep all passed patch testing with no visible effects on the animal skin.

8.2 Rate of Powder Loss on Each Type of Animal

All data were plotted on separate scatter graphs to show patterns of loss (FIGS. 7 to 10).

Figure 11:
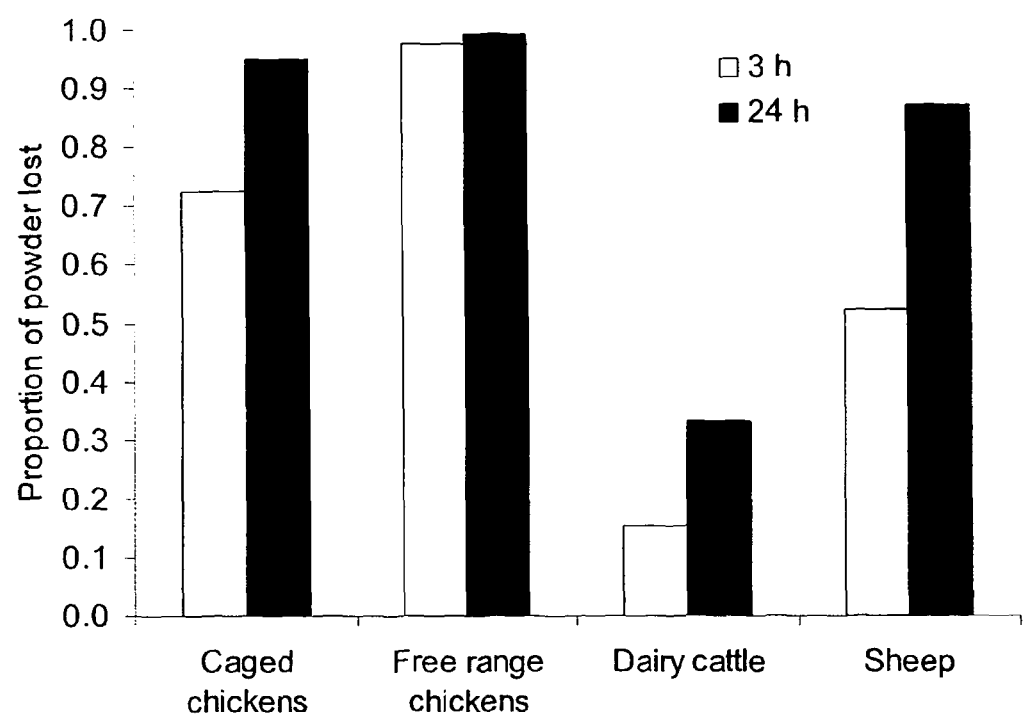

The rates of loss (FIG. 11) and the initial level of adhesion were different between the four animal groups. Sheep took up the most powder initially but lost a greater proportion of powder over time than cattle. Free range chickens took up the least amount of powder and exhibited the fastest rate of powder loss of all the categories; but small quantities could still be detected at 24 h post application.

Statistical analysis showed that the proportion of powder lost between 0 and 3 h and between 0 and 24 h were significantly different between one or more groups (0-3 h: Kruskal obs=24.96, Kruskal crit=7.82, DF=3, P<0.0001; 0-24 h: Kruskal obs=29.49, Kruskal crit=7.81, DF=3, P<0.0001). Pair-wise comparisons showed that the proportion of powder lost by 3 h was significantly higher for free range chickens than any other group but no other groups were significantly different. 24 h pair-wise comparisons showed that the proportion of powder lost was significantly higher for free range hens than sheep or cattle, significantly higher for caged hens than cattle and no other groups were significantly different.

The initial amount of powder taken up was significantly different between one or more groups (ANOVA: $F_{3,38}$=11.59, P<0.0001). Pair-wise comparisons showed that sheep took up greater quantities than either hen group and that cattle took up greater quantities than free range hens (see Table 6).

TABLE 6

Results of Tukey (HSD) test: analysis of the differences between the categories (initial powder taken up) with a confidence interval of 95%

| Contrast | Difference | Standardized difference | Critical value | Pr > Diff | Significantly Different? |
|---|---|---|---|---|---|
| Sheep vs Free range | 0.794 | 5.143 | 2.697 | <0.0001 | Yes |
| Sheep vs Caged hen | 0.740 | 4.669 | 2.697 | 0.000 | Yes |
| Sheep vs Cattle | 0.317 | 2.052 | 2.697 | 0.189 | No |
| Cattle vs Free range | 0.477 | 3.091 | 2.697 | 0.019 | Yes |
| Cattle vs Caged hen | 0.424 | 2.671 | 2.697 | 0.053 | No |
| Caged hen vs Free range | 0.053 | 0.337 | 2.697 | 0.987 | No |
| Tukey's d critical value | | | 3.814 | | |

8.3 Whole Treatment of Caged Hens

Figure 12:
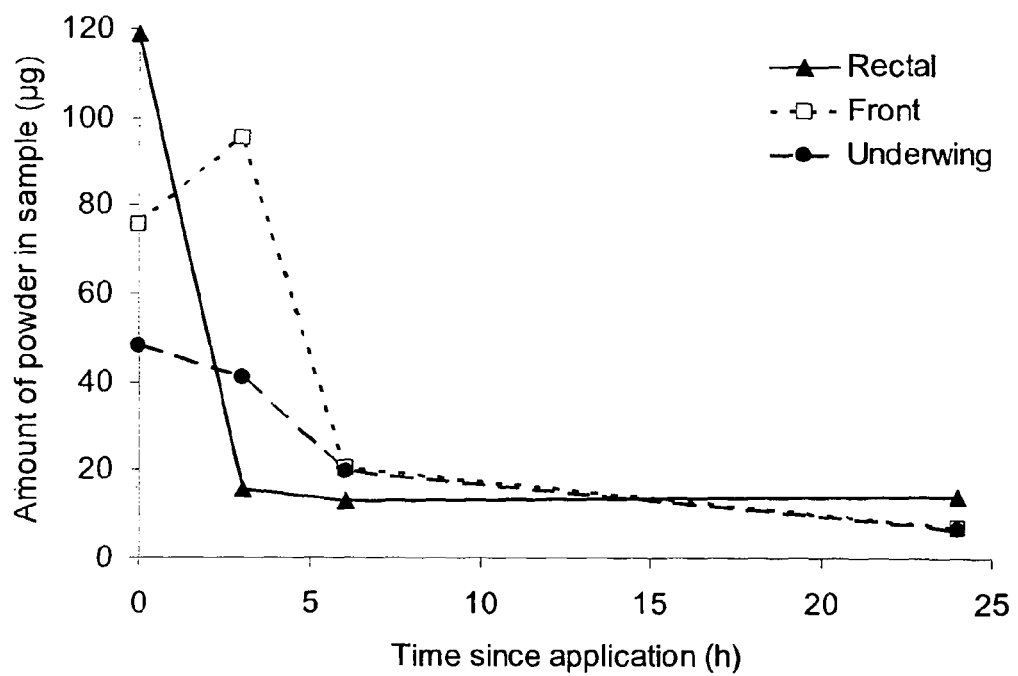

Only two birds received a whole body application so this was not a fully replicated study. However it gave initial indications that carnauba wax powder would adhere to different areas and it could be detected on the rectal area, breast and under the wing at 24 h post application (FIG. 12).

9 Discussion

Uptake and retention of powder on sheep and cattle was superior to that of hens. In terms of initial uptake it is likely that the carnauba wax powder adheres better to the oily hair/wool by means of lipid-lipid interactions as well as static attraction, than it does to feathers. Also retention was better, possibly because treatment locations on the sheep and cattle were at the top of the shoulders which experience limited movement or brushing up against other surfaces. On hens, movement of feathers would be frequent, especially if the wings are moved and the hens frequently brush against each other and the cage interior (for caged hens). Free range hens were also observed to take dust baths with their wings held out. The reason for initial adherence being better on caged hens than free range is not completely clear but free range hens had thicker layers of feathers under the wing than caged hens and this may have reduced the efficacy of the swabbing technique on free range hens; or adherence is better on the skin of the hens than directly on the feathers.

The invention claimed is:

1. A method of producing a dry powder composition comprising the steps of
   i) admixing at least one chemical organic compound that is capable of controlling the population of an animal-infesting arthropod species with a liquid hydrophobic carrier substance formed from hydrophobic particles selected from carnauba wax, beeswax, Chinese wax, shellac wax, spermaceti wax, candelilla wax, castor wax, ouricury wax and rice bran wax,
   ii) allowing the mixture of the liquid hydrophobic carrier substance and the at least one chemical compound of step i) to cool to a solid state; and
   iii) at least one of milling and micronising the mixture to form a dry powder;
   wherein the dry powder composition is effective in controlling at least one population of animal-infesting arthropod species and comprises composite particles, and wherein the composite particles have a volume mean diameter in the range from 10 microns to 200 microns and comprise:

i) hydrophobic particles selected from carnauba wax, beeswax, Chinese wax, shellac wax, spermaceti wax, candelilla wax, castor wax, ouricury wax and rice bran wax, wherein the particles are configured to adhere to the cuticle of one or more species of animal-infesting arthropod and wherein the particles are configured to adhere to fur, hair, feathers or skin of an animal; and ii) at least one organic chemical compound admixed therewith, wherein the said organic chemical is capable of controlling the population of at least one animal-infesting arthropod species on livestock, domestic pets, poultry, game birds and ornamental birds.

* * * * *